(12) United States Patent
Rajek et al.

(10) Patent No.: US 12,369,897 B2
(45) Date of Patent: Jul. 29, 2025

(54) SURGICAL RETRACTORS AND METHODS OF USING THE SAME

(71) Applicant: Alphatec Spine, Inc., Carlsbad, CA (US)

(72) Inventors: Andrew W. Rajek, Escondido, CA (US); Steven Vidmar, Carlsbad, CA (US); James Lee, Vista, CA (US); David Considine, Carlsbad, CA (US); Graham Witherby, Carlsbad, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 0 days.

(21) Appl. No.: 17/738,998

(22) Filed: May 6, 2022

(65) Prior Publication Data

US 2022/0354477 A1 Nov. 10, 2022

Related U.S. Application Data

(60) Provisional application No. 63/186,008, filed on May 7, 2021.

(51) Int. Cl.
*A61B 17/02* (2006.01)
*A61B 90/00* (2016.01)

(52) U.S. Cl.
CPC .. *A61B 17/0206* (2013.01); *A61B 2090/0807* (2016.02)

(58) Field of Classification Search
CPC ............ A61B 17/0206; A61B 17/0218; A61B 2090/061; A61B 2090/0807; A61B 2090/0811
See application file for complete search history.

(56) References Cited

U.S. PATENT DOCUMENTS

| 5,928,139 A | * | 7/1999 | Koros ................ A61B 17/0206 600/245 |
| 6,342,036 B1 | * | 1/2002 | Cooper ............. A61B 17/0293 600/232 |
| 9,028,522 B1 | * | 5/2015 | Prado ................. A61B 17/0206 606/191 |

(Continued)

FOREIGN PATENT DOCUMENTS

| DE | 202009005768 U1 | * | 7/2009 | ......... A61B 17/0206 |
| DE | 202020003344 U1 | * | 10/2020 | ............. A61B 17/02 |
| WO | WO-2016153942 A1 | * | 9/2016 | ......... A61B 17/0206 |

OTHER PUBLICATIONS

Written Opinion of the International Searching Authority from related pending international application PCT/US2022/028132, dated Oct. 24, 2023.

*Primary Examiner* — Eduardo C Robert
*Assistant Examiner* — Anna V. Little
(74) *Attorney, Agent, or Firm* — Robert Winn

(57) ABSTRACT

Disclosed herein are surgical retractors and methods of using such surgical retractors where the surgical retractors include a base portion and two retractor blades. The base portion has (a) two extensions, each extension having a receiving area, and (b) and one or more engagement portions. Each retractor blade includes both a blade portion with proximal and distal ends and an arm portion extending from the proximal end of the blade portion. Each arm portion is received by a respective receiving area.

28 Claims, 11 Drawing Sheets

(56) References Cited

U.S. PATENT DOCUMENTS

| | | | |
|---|---|---|---|
| 2004/0087833 A1* | 5/2004 | Bauer | A61B 17/0218 600/201 |
| 2010/0081885 A1* | 4/2010 | Wing | A61B 17/0206 600/215 |
| 2010/0222644 A1* | 9/2010 | Sebastian | A61B 17/0206 600/228 |
| 2012/0323080 A1* | 12/2012 | DeRidder | A61B 17/0218 600/215 |
| 2013/0261401 A1* | 10/2013 | Hawkins | A61B 17/025 600/213 |
| 2014/0172002 A1* | 6/2014 | Predick | A61B 17/025 606/191 |
| 2014/0336471 A1* | 11/2014 | Pfabe | A61B 17/0293 600/231 |
| 2015/0351738 A1* | 12/2015 | Perrow | A61B 1/32 600/233 |
| 2016/0192922 A1* | 7/2016 | Friedrich | A61B 90/30 600/214 |
| 2016/0317137 A1* | 11/2016 | Predick | A61B 17/0206 |
| 2017/0143325 A1* | 5/2017 | Lynn | A61B 1/07 |
| 2017/0231613 A1* | 8/2017 | Casey | A61F 2/30771 600/213 |
| 2017/0238918 A1* | 8/2017 | Predick | A61B 17/7077 |
| 2017/0333023 A1* | 11/2017 | Adams | A61B 17/0206 |
| 2019/0021715 A1* | 1/2019 | O'Connell | A61B 17/0293 |
| 2019/0142480 A1* | 5/2019 | Woolley | A61B 1/32 606/86 A |
| 2019/0298328 A1* | 10/2019 | Popejoy | A61B 17/0293 |
| 2019/0307439 A1* | 10/2019 | Chhit | A61B 1/042 |
| 2020/0015799 A1* | 1/2020 | Tsubouchi | A61B 17/0206 |
| 2021/0085306 A1* | 3/2021 | Clauss | A61B 17/025 |

\* cited by examiner

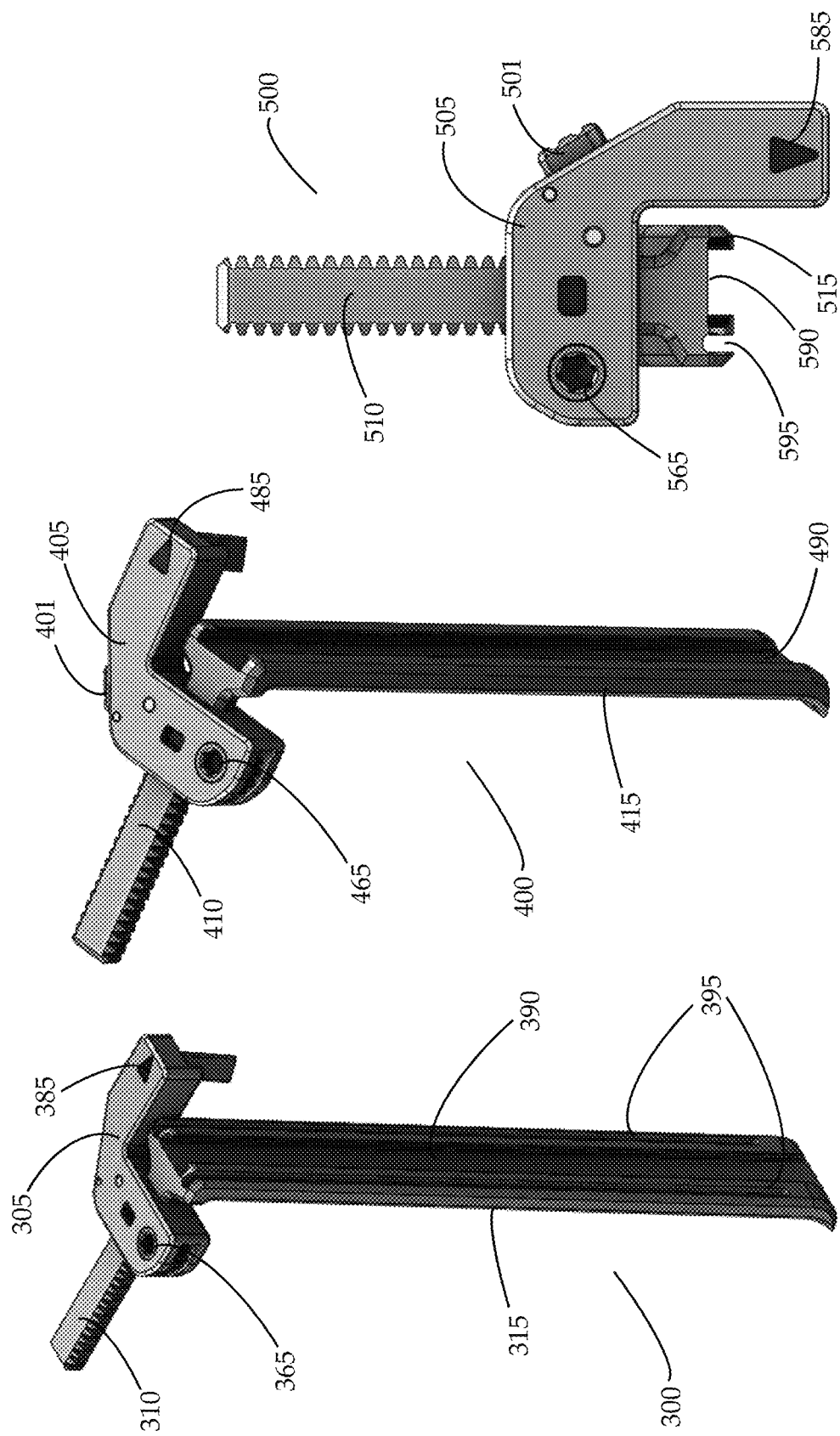

SURGICAL RETRACTORS AND METHODS OF USING THE SAME

RELATED APPLICATION

This application claims priority to U.S. Provisional Application No. 63/186,008, filed May 7, 2021, the entirety of which is incorporated herein by reference.

BACKGROUND

The present disclosure relates to surgical retractors configured to provide access to a surgical site, such as a portion of a patient's spine. Also disclosed herein are methods of using such surgical retractors in surgical procedures, such as a spinal surgery.

SUMMARY

Disclosed herein are surgical retractors and methods of using such surgical retractors where the surgical retractors include a base portion and two retractor blades. The base portion has (a) two extensions, each extension having a receiving area, and (b) and one or more engagement portions. Each retractor blade includes both a blade portion with proximal and distal ends and an arm portion extending from the proximal end of the blade portion. Each arm portion is received by a respective receiving area.

Each receiving area may include a ratchet mechanism that engages with and locks the arm portion relative to the base portion. In some embodiments, the arm portion includes ratchet teeth to engage the ratchet mechanism. In some embodiments, the receiving areas can include an advancement mechanism that when rotated adjusts the position of the arm portion relative to the base portion.

According to some embodiments, the retractor blades consist of a unitary piece. In some embodiments, the retractor blades are functionally integral. In some embodiments, the blade portion is orthogonal to the arm portion, each blade portion is parallel to the other blade portion, and the arm portions are parallel to the base portion. In some embodiments, the retractor is configured to maintain such orthogonality and parallel orientation even as the two retractor blades are adjusted relative to the base portion.

Some embodiments include an alignment feature to indicate whether the retractor is properly oriented relative to a target site, such as a patient's disc space. In some embodiments, a proper orientation is lateral approach that is orthogonal to the disc space. In some embodiments, the alignment feature is radiographically identifiable and is positioned at a proximal end of one or both of the blade portions.

Some embodiments of surgical retractors are configured for use when the patient is in the prone position. Some embodiments allow for use when the patient is in the supine or lateral decubitus position.

According to some embodiments, one or both blade portions include a central channel in order to secure to the blade portion a light cable, anchoring mechanism, blade extender, or other useful tool. Some embodiments include at least one lateral channel that may be used in conjunction with a bone anchor.

According to some embodiments, the cross section of the retractor blades when together is generally circular. In some embodiments, the cross section is general oval-shaped. Whether circular-shaped or oval-shaped, the blades may be configured to slide over a dilator when being advanced toward the surgical site.

Also disclosed herein are methods of using a surgical retractor. Some methods include making an incision in a patient's skin at a position lateral to the patient's spine, locating a surgical site on the spine, inserting the posterior and anterior retractor blades of a two-bladed surgical retractor—which may be a surgical retractor according to the present disclosure—advancing the surgical retractor toward the surgical site, positioning the distal end of the posterior retractor blade at a posterior position of the surgical site, anchoring the posterior retractor blade at the posterior position, and enlarging the surgical corridor.

In some embodiments, locating the surgical site on the spine includes advancing a K-wire toward the surgical site and embedding a distal end of the K-wire into a tissue at the surgical site, and sequentially advancing at least an inner dilator and at least an outer dilator—both of which may have a cross section that is circular or oval in shape—over the K-wire toward the surgical site. In some embodiments, at least one of the inner and outer dilators comprises at least one electrode and is configured to provide neural monitoring, such as plexus mapping, as the dilator is advanced toward the surgical site.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be better understood when read in conjunction with the following drawings wherein like structure is indicated with like reference numerals and in which:

FIG. 9 is a perspective view of one embodiment of an auxiliary retractor blade according to the present disclosure;

FIG. 10 is a perspective view of another embodiment of an auxiliary retractor blade according to the present disclosure;

FIG. 11 is a top view of yet another embodiment of an auxiliary retractor blade according to the present disclosure;

DETAILED DESCRIPTION

The present disclosure relates to surgical retractors and specifically retractors configured for use in spinal surgeries. Retractors are designed to not simply allow access to a surgical site, but they are further designed to accommodate the particular issues encountered when accessing those surgical sites. To that end, the surgical retractors disclosed herein as well as the methods for using them are particularly suited to accessing the spine of a patient using a lateral approach. Some embodiments are more particularly suited a lateral approach with the patient in a prone position. Some embodiments are more particularly suited a lateral approach with the patient in a lateral decubitus position. Some embodiments are more particularly suited a lateral approach with the patient in a supine position. Although some embodiments are suited for a lateral approach, other approached are also contemplated because the advantageous features of the disclosed retractors lend themselves to other approaches.

Figure 1:
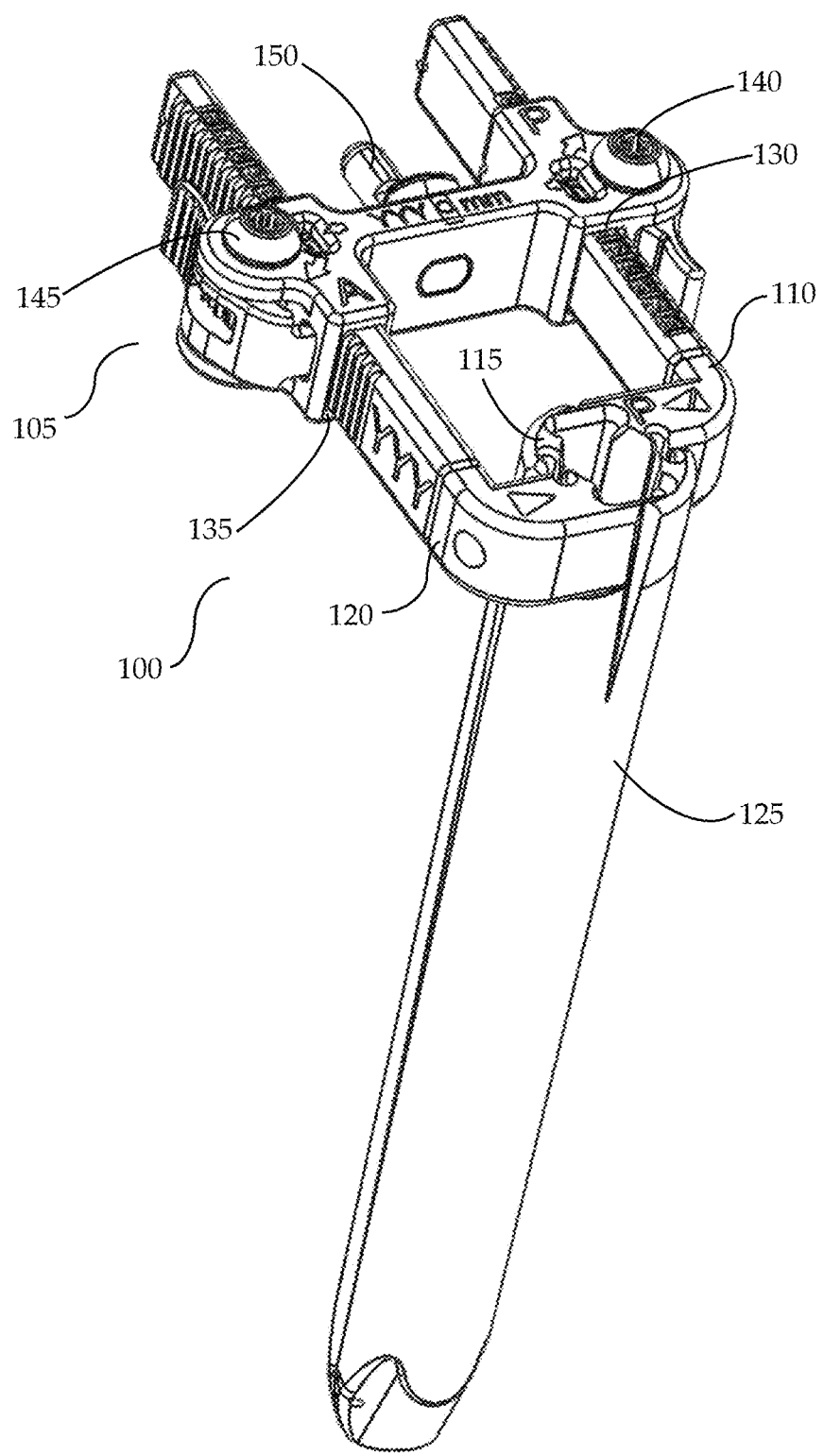
FIG. 1 is a perspective view of a surgical retractor according to the present disclosure.

FIG. 1 illustrates one embodiment of a retractor 100 that includes a base portion 105 having two extensions, a posterior retractor arm 110, a posterior retractor blade 115, an anterior retractor arm 120, and an anterior retractor blade 125. Base portion 105 includes two receiving areas 130, 135—one on each extension. Receiving areas 130, 135 are configured to receive each of the retractor arms. Receiving area 130 is configured to receive posterior retractor arm 110, and receiving area 135 is configured to receive anterior retractor arm 120. Each retractor arm 110, 120 may be removably received by each receiving area 130, 135, or they may include a pin at their respective ends (or some other retaining means) to prevent the arms from being separated from base portion 105. Removability may be desired in order to have the option of quickly opting for a different retractor blade in the posterior and/or anterior position. Base portion 105 is illustrated in greater detail in FIG. 5.

According to some embodiments, retractor 100 is positioned for use in a lateral approach of the lumbar spine during which the patient may be in a prone position, lateral decubitus position, or supine position. In some embodiments, retractor 100 will be positioned with retractor blades 115, 125 forming an orthogonal corridor to the patient's disc space—with posterior blade 115 being posterior to the disc space and anterior blade 125 being anterior to the disc space—in which case base portion 105 will be positioned outside the patient and posterior to the disc space. Other configurations and arrangements are possible, though it has been found that this arrangement provides desired stability with limited interference to the surgical corridor.

Each receiving area includes an adjustment mechanism— 140 and 145, respectively—configured to both hold each retractor arm in a fixed position relative to base portion 105 and to allow for incremental adjustment of each retractor arm. Adjustment mechanisms 140, 145 are configured to operate independently of each other. In some embodiments, the two mechanisms are configured to at least partially operate in conjunction by either simultaneously adjusting the two retractor arms and/or by simultaneously releasing each retractor arm so they can freely move relative to base portion 105. Adjustment mechanisms 140, 145 may take the form of any suitable mechanism capable of maintaining the position of retractor arms 110 and 120 fixed relative to base portion 105. In some embodiments, adjustment mechanisms 140, 145 are additionally capable of adjusting the position of retractor arms 110 and 120 fixed relative to base portion 105. In the illustrated embodiment, adjustment mechanisms 140, 145 are ratchet mechanisms that engage corresponding ratchet teeth on each retractor arm.

Base portion 105 further includes an engagement portion 150 extending from base portion 105, which is configured to allow retractor 100 to be releasably secured to a support structure, such as an A-arm that is itself secured to another support structure, such as a bed frame or patient support structure.

Each retractor arm and its associated retractor blade may comprise a unitary piece, may be secured or attached to each to functionally achieve a unitary piece, or be releasably secured to each other. In this embodiment, each retractor arm and its blade is manufactured to be unitary. One advantage of being unitary or functionally unitary is added strength and stability. Such stability is needed to maintain the position of the retractor arm and prevent unwanted movement.

In this illustrated embodiment, various components are configured to be generally orthogonal or generally parallel to each other. For example, base portion 105 can be described as having two extensions along a first plane with each retractor arm located also in the first plane and configured to be maintained in the first plane even as they are adjusted relative to base portion with each are retractor being parallel to the other retractor arm. Similarly, engagement portion 150 extends from base portion 105 in the first plane. Posterior blade 115 and anterior blade 125 are each orthogonal to the first plane and are parallel to each other. The respective orientations are maintained even while adjusting or enlarging the surgical corridor, which requires that one or both of the retractor blades be adjusted relative to base portion 105.

In the illustrated embodiment, engagement portion 150 is shown as extending orthogonally from base portion 105; however, in some embodiments, engagement portion 150 extends at an angle. For example, if engagement portion 150 defines an axis, and if base portion defines a plane, the angle between the axis and the plane is 0° in the illustrated embodiment but may be any suitable angle from about −45° to about 90°, such as about −30°, about −15°, about 0°, about 15°, about 30°, or about 45°.

Figure 2:
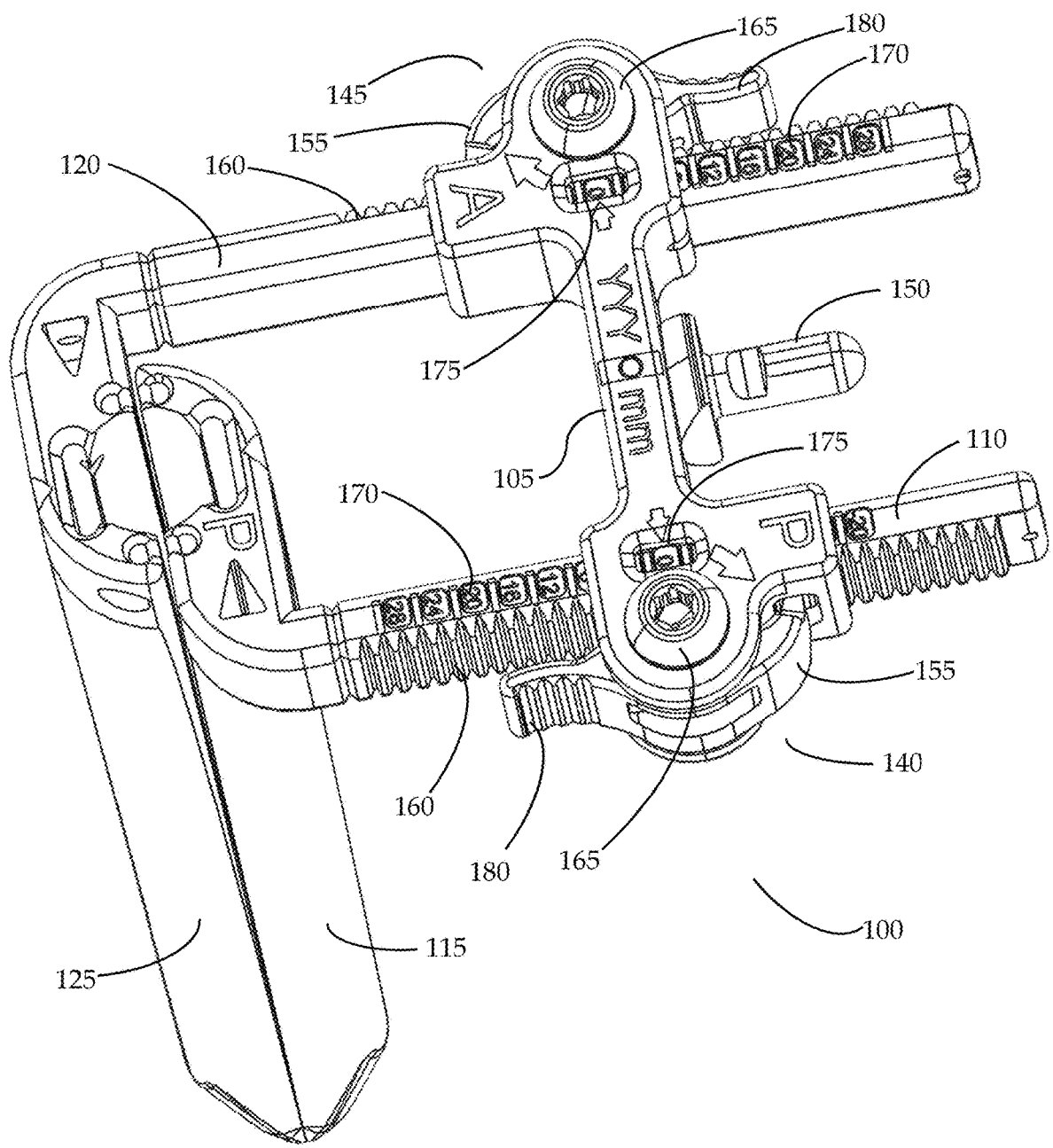
FIG. 2 is another perspective view of the embodiment shown in FIG. 1.

FIG. 2 illustrates retractor 100 at a slightly different angle to better illustrate adjustment mechanisms 140, 145 each of which includes a pawl 155 configured to engage a set of teeth 160 on each retractor arm. Each adjustment mechanism further includes a toothed shaft 165 (at least partially visible in FIG. 5) that when rotated clockwise moves the retractor arm either proximally (as is the case with proximal retractor arm 110) or anteriorly (as is the case with anterior retractor arm 120). As retractor arms 110, 120 are advanced relative to base portion 105, markings 170 on each retractor arm are visible through indicator windows 175. In some embodiments, markings 170 are placed at increments of 0.5 mm, 1 mm, 2 mm, 3 mm, 4 mm, or some value between those values. Markings 170 correlate to the size and spacing of teeth 160 along retractor arms 110, 120 and indicate the displacement of each retractor arm from a "zero" position.

Advancing retractor arms 110, 120 expands the surgical corridor. Retractor arms 110, 120 may also be released or allowed to return to their original positions as to allow adjustment of the surgical corridor or removal of retractor blades 115, 125 from the surgical site by pressing one or both of levers 180, which disengages pawls 155 from teeth 160. By holding down one lever (either on the posterior or anterior side) while rotating the toothed shaft on the other side, a user can translate both anterior arm 120 and posterior arm 110 in unison. This may be desirable when a user desires to move retractor 100 to improve its positioning but where the user does not want to adjust the surgical support to which retractor 100 is clamped or secured.

Figure 3:
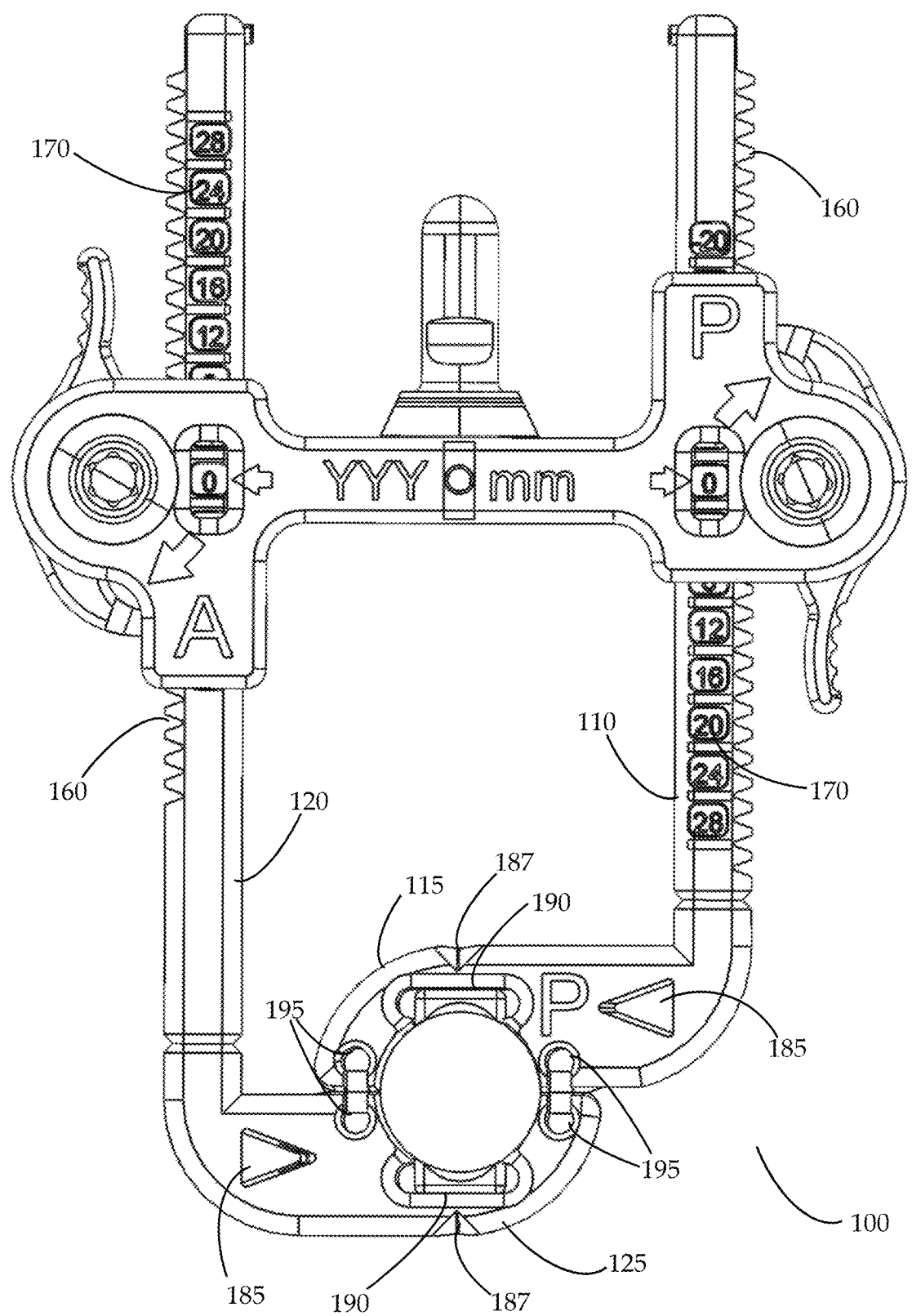
FIG. 3 is a top down view of the surgical retractor shown in FIG. 1.

FIG. 3 illustrates retractor 100 from above or, in other words, along the surgical corridor created by posterior retractor blade 115 and anterior retractor blade 125. This perspective also illustrates that posterior retractor arm 110 and anterior retractor arm 120 each include an alignment feature 185 and that the respective proximal ends of posterior blade 115 and anterior blade 125 each include additional alignment feature 187. In this embodiment, alignment feature 185 is a triangular bore that extends from a top surface of each retractor arm to a bottom surface. Additional alignment feature 187 is an angled cut on the outer surface of each blade. Both alignment feature 185 and additional alignment feature 187 are configured to provide a surgeon with an indication of the orthogonality of retractor 100 relative to the patient's disc space. Such orthogonality is achieved by creating an incision in a patient to access the disc space from a lateral approach, positioning retractor 100 in the incision, and then confirming the position of retractor 100 using radiographic images of the disc space. The indication of orthogonality is achieved when the alignment features 185 are fully visible in the radiographic image, which image has been arranged to look directly at the target space along a perspective orthogonal to that disc space.

Although illustrated as triangular in shape, alignment features 185 may be formed using any other suitable shape, such as a circle, a square, etc. And although alignment features 185 in this embodiment are bores that extend from a top surface to a bottom surface, partial bores may provide the desired amount of radiolucency. Alternatively, if retractor arms 110, 120 are somewhat radiolucent themselves, alignment features 185 may comprise radiopaque markers, such as a radiopaque material embedded or applied to retractor arms 110, 120.

FIG. 3 also illustrates that retractor blades 115, 125 each include a central channel 190 as well as two lateral channels 195. In some embodiments, central channel is configured to receive at least one of a light cable, a tissue shim, an intradiscal shim, an anchoring shim, a blade extender, or any other suitable device. In some embodiments, at least one of lateral channels 195 is configured to receive an anchor device, such as a bone screw the head of which mates with lateral channel 195, a light cable, tissue shim, auxiliary retraction device, etc.

Looking down the opening created between retractor blades 115, 125 highlights the circular shape of the opening. In some embodiments, however, the opening will have other shapes, such as oval or oblong. Although not illustrated, such non-circular shapes are achieved in some embodiments by expanding the width of retractor blades 115, 125 compared to their depth or thickness.

In some embodiments, the shape of the opening between retractor blades 115, 125 may be determined by the shape of the type of implant intended to be surgically implanted in a patient's body. For example, wider implants may require a wider surgical corridor, but rather than simply expanding the corridor in all directions, using oval-shaped blades will enlarge the corridor in one direction without requiring a larger corridor in all directions thereby reducing trauma to surrounding tissue and nerves.

In some embodiments, the shape of the opening is determined by the shape of dilators that are used to chart the path toward the surgical site and create the surgical corridor. For example, where cylindrical dilators are used, using a retractor with circular-shaped blades may provide the best engagement to allow for a working corridor to be created, whereas oval-shaped dilators may require or at least suggest the use of a retractor whose blades together form an oval-shaped opening or corridor.

Figure 4:
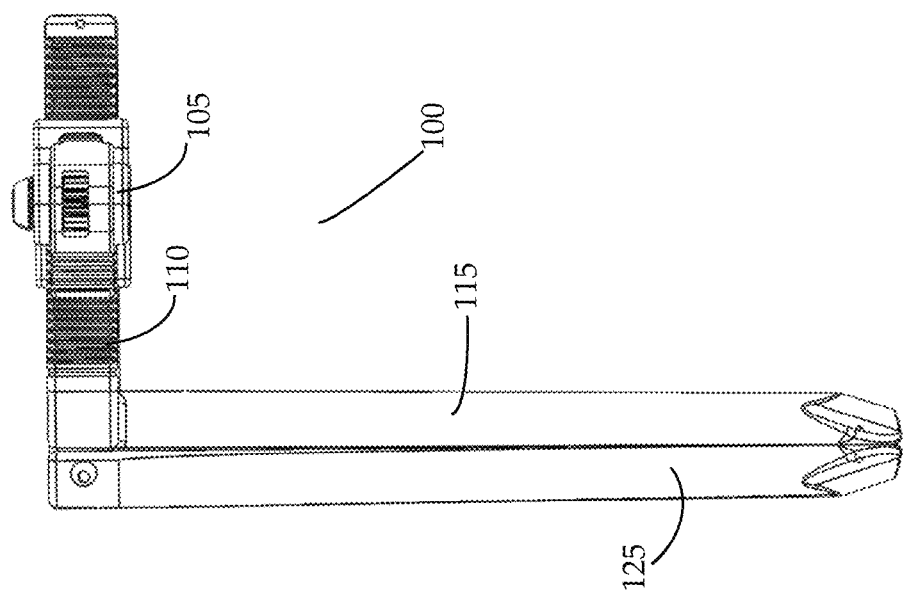
FIG. 4 is a side view of the surgical retractor shown in FIG. 1.

FIG. 4 is a side or lateral view of retractor 100 and illustrates the desired orthogonality between retractor arms 110, 120 and retractor blades 115, 125, which is achieved in part by securely maintaining retractor arms 110, 120 in line with base portion 105. FIG. 4 also illustrates the generally cylindrical shape of retractor blades 115, 125 especially when blades 115, 125 are positioned to abut each other; however, and as illustrated, some embodiments include retractor blades that taper toward the distal end. In some embodiments, such tapering is limited to the outside surfaces of the retractor blade. In other words, the inside surfaces of the retractor blades together maintain a consistent cylindrical path along their respective lengths.

Figure 5:
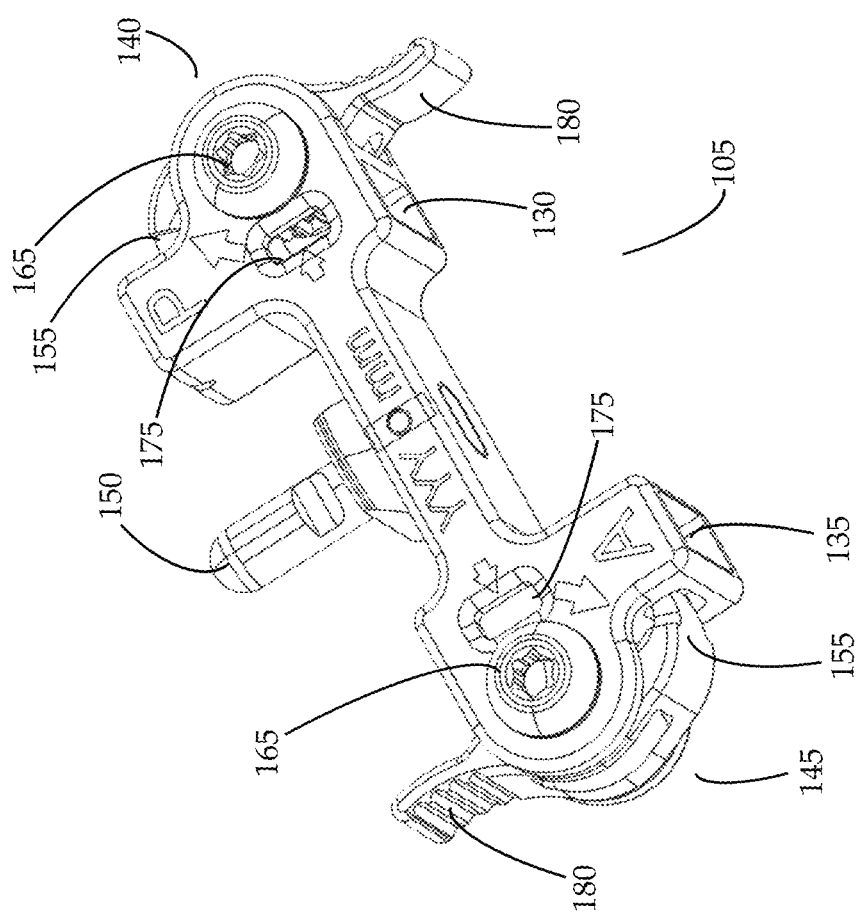
FIG. 5 is a perspective view of a base portion, which is a component of the surgical retractor shown in FIG. 1.

FIG. 5 illustrates base portion 105 in isolation. Without retractor arm 110 inserted through receiving area 130, it is possible to see the toothed portion of toothed shaft 165 through indicator window 175. For ease of use, each end or extension of base portion is labeled with either an "A" for "anterior" or a "P" for posterior, which indicates not only which retractor arm to insert into which receiving area but also provides a ready reminder for how to position retractor 100 relative to the patient and, in particular, the disc space to be accessed.

Figure 6:
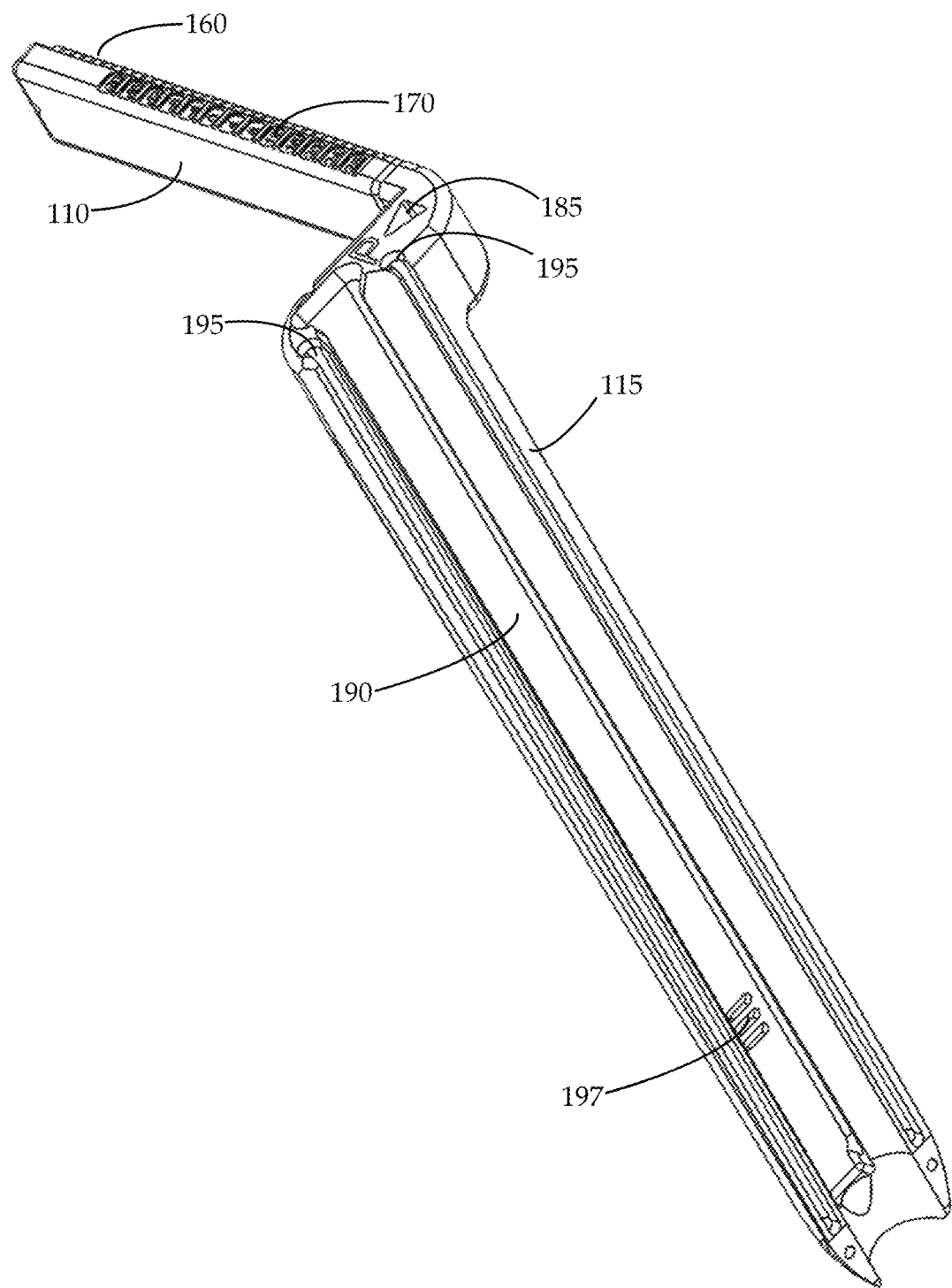
FIG. 6 is a perspective view of a surgical arm and blade, which is a component of the surgical retractor shown in FIG. 1.

FIG. 6 illustrates posterior retractor arm 110 and posterior retractor blade 115, which in this embodiment are constructed to form a unitary piece. In some embodiments, the retractor arm and blade consist of a single unit. In some embodiments, the arm and blade are irreversibly secured to each other to essentially form a single unit. In some embodiments, the blade and arm are reversibly attached to each other.

Central channel 190 is shown as extending almost the entire length of blade 115 with one opening at the proximal end of blade 115. In some embodiments, central channel 190 extends the full length of blade 115 meaning that it opens at both the proximal and distal ends of blade 115. In this illustrated embodiment, central channel 190 includes depressions 197 that are configured to provide various locking or stopping points for tools that are inserted into the surgical corridor along central channel 190. For example, an intradiscal shim may be locked in position relative blade 115 when an extension or tab on the shim is able to extend into one of depressions 197. Although not illustrated in FIG. 7, similar depressions may be incorporated into the central channel of anterior retractor blade 125.

Figure 7:
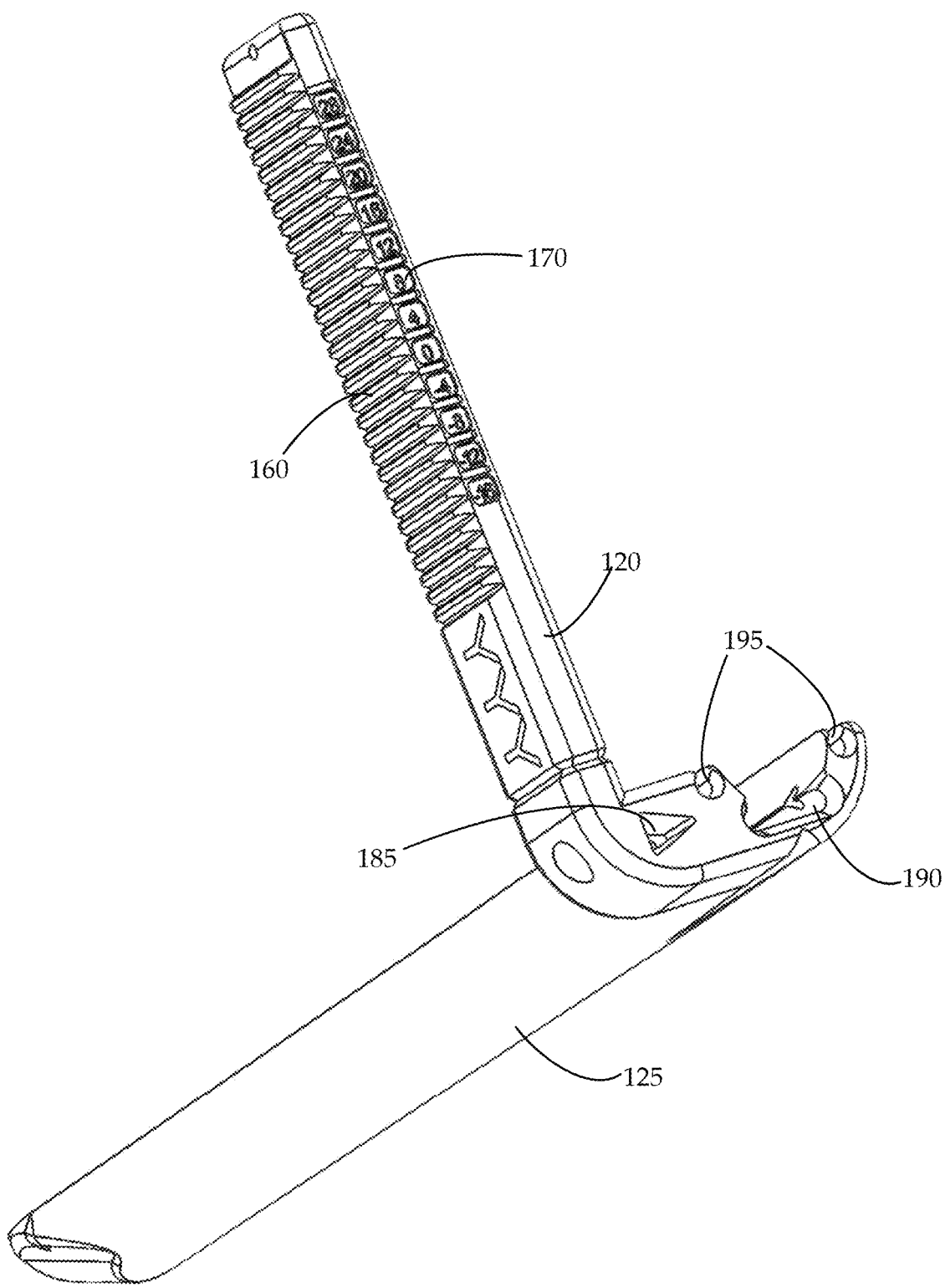
FIG. 7 is a perspective view of a surgical arm and blade, which is a component of the surgical retractor shown in FIG. 1.

FIG. 7 illustrates anterior retractor arm 120 and anterior retractor blade 125 that are shown as constructed to form a unitary piece. Similar to arm 110 and blade 115, arm 120 and blade 125 may consist of a single unit or may be secured to result in a single unit or may be reversibly secured to each other.

Methods for using surgical retractor 100 and similar retractors consistent with the present disclosure include a number of preparation steps. In some embodiments, such preparation begins with positioning a patient in a prone position, a lateral decubitus position, a supine position, or any other suitable patient position. Subsequent preparation includes identifying an incision point for accessing a desired surgical site, creating an incision, and advancing an instrument guide—such as a guide wire or a K-wire—to the surgical site. The instrument guide may be advanced through at least a portion of the psoas muscle in order to achieve a transpsoas procedure.

With initial access to the surgical site established, some embodiments include advancing one or more sequential dilators along the instrument guide through the incision and down to the surgical site. One or more of the sequential dilators may be configured to provide for neural monitoring and/or nerve detection. The sequential dilators may have a circular cross section or an oval-shaped cross section. In some embodiments, a suitable retractor—such as surgical retractor 100—is advanced over the outermost dilator until the distal end of the retractor contacts or is sufficiently near the surgical site or disc space, after which the dilator(s) may be removed so as to allow retractor 100 to create a surgical corridor to access the surgical site.

Once positioned, retractor 100 may be secured to a surgical support, such as A-arm that is secured to a frame, surgical bed, or surgical table. In some embodiments, one of the surgical retractor's blades—such as posterior blade 115—is positioned posteriorly of the disc space. Such positioning may be accomplished by adjusting the surgical support (e.g., an A-arm) or by manipulating adjustment mechanism 140 to move posterior blade 115 posteriorly. Once properly positioned, an anchor or intradiscal shim is advanced down into the surgical corridor along either central channel 190 or one of lateral channels 195 to be placed in either bone or the intradiscal space to fix posterior blade 115 relative to the disc space.

A surgeon or user then operates one or both of adjustment mechanisms 140, 145 to expand the surgical corridor by moving anterior blade 125 anteriorly until a desirably sized surgical corridor is created at which point anterior blade 125 may be anchored using an anchor screw or an intradiscal shim or any other suitable anchoring mechanism.

Figure 8:
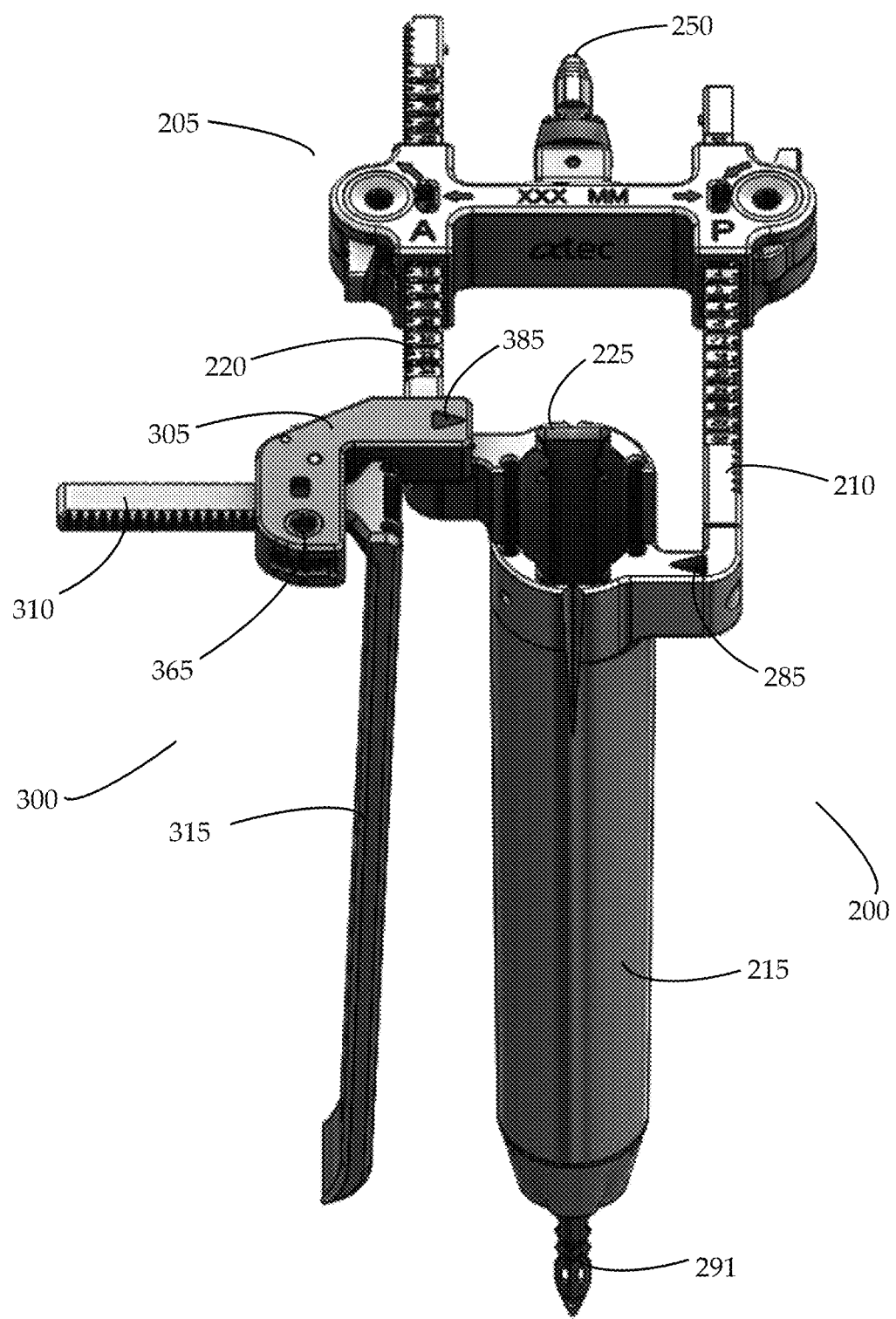
FIG. 8 is a perspective view of a surgical retractor according to the present disclosure that includes an auxiliary retractor blade.

FIG. 8 illustrates an embodiment of a surgical retractor 200, which in many respects is similar to retractor 100; however, it will be noticed that the relative positions of posterior retractor blade 215 and anterior retractor blade 225 are reversed compared to posterior retractor blade 115 and anterior retractor blade 125. In some embodiments, one orientation is preferable over the other orientation. This embodiment is also illustrated with an intradiscal shim 291 positioned within the channel of posterior blade 215. As is discussed elsewhere in this document, the one or more channels in the retractor blades may be configured to receive any number of attachments or accessories, such as tissue shims of various sizes and shapes, intradiscal shims, light cables, bone anchors, etc.

FIG. 8 also illustrates that a surgical retractor according to the present disclosure, such as retractor 200, may be configured to receive one or more modular blade assemblies, such as modular blade assembly 300 that includes a base portion 305, a blade arm 310, and an auxiliary blade 315. Modular blade assembly 300 includes many features found on retractors 100 and 200, such as an adjustment mechanism 365 that, when rotated, adjusts the position of auxiliary blade 315 relative to posterior blade 215 and anterior blade 225, which adjustment increases or decreases the surgical corridor created by the various retractor blades. Modular blade assembly 300 is designed to snap onto or otherwise securely attached to anterior blade arm 220. Some embodiments of modular blade assemblies, such as will be discussed in greater detail below, are configured to be snapped onto or otherwise securely attached to posterior blade arm 210.

Blade arm 310 is movable with respect to base portion 305 and may, in some embodiments, be entirely removed from base portion 805. This modularity allows for the use of different base portions with different blades. Different designs for base portions and different designs for blades are discussed in greater detail below. In some embodiments, a set of instruments for a modular blade assembly includes (1) a single base portion and two or more distinct retractor blades, (2) two or more base portions and a single retractor blade, or (3) two or more base portions and two or more retractor blades. In some embodiments, it may be advantageous to use different arrangements of base portions and/or retractor blades during a single procedure as the needs of the user change over the course of the procedure.

Modular blade assembly also includes an alignment feature 385. In this embodiment, alignment feature 385 is a triangular-shaped through-hole in base portion 305 that aligns with an alignment feature located on anterior blade arm 220 (not illustrated, though similar to alignment feature 285 of posterior blade arm 210). This alignment is designed to not inhibit a user's ability to use the alignment feature on retractor 200. In some embodiments, alignment feature 385 is designed to enhance the functionality of the alignment feature on the retractor arm. Although in this illustrated embodiment, alignment feature 385 is shaped and sized to be substantially the same as the underlying alignment feature, in some embodiments, alignment feature 385 has a different shape from the underlying alignment feature and/or is larger or smaller than the underlying alignment feature.

FIGS. 9-11 illustrate three different embodiments of modular blade assemblies each of which is configured for attachment to an anterior blade arm of a retractor according to the present disclosure; however, a skilled artisan will understand that the features of these disclosed embodiments could be equally applied to modular blade assemblies that are configured to be attached to a posterior blade arm.

FIG. 9 illustrates that auxiliary blade 315 of modular blade assembly 300 includes both a central channel 390 as well as two lateral channels 395. In some embodiments, central channel 390 is configured to receive any one of a tissue shim, intradiscal shim, and/or a light cable. In some embodiments, lateral channels 395 are configured to receive at least a portion of a bone anchor so as to anchor or secure in position auxiliary blade 315 relative to a surgical site.

FIG. 10 illustrates an embodiment of a modular blade assembly 400 that is similar to modular blade assembly 300; however, auxiliary blade 415 includes only a central channel 490 and not lateral channels. Also visible in FIG. 10 is the presence of release mechanism 401 that is configured to provide a quick release for blade arm 410. In some embodiments, release mechanism 401 operates by sliding back and forth. In some embodiments, release mechanism 401 operates as a push button that is depressed to release blade arm 410. When release mechanism 401 is activated, blade arm 410 may slide freely relative to body portion 405.

FIG. 11 illustrates an embodiment of a modular blade assembly 500 that is similar to modular blade assemblies 300 and 400; however, auxiliary blade 515 includes a central channel 590 and only one lateral channel 595 to the left of central channel 590. In some embodiments, lateral channel 595 is positioned to the right of central channel 590.

Figures 12, 13:
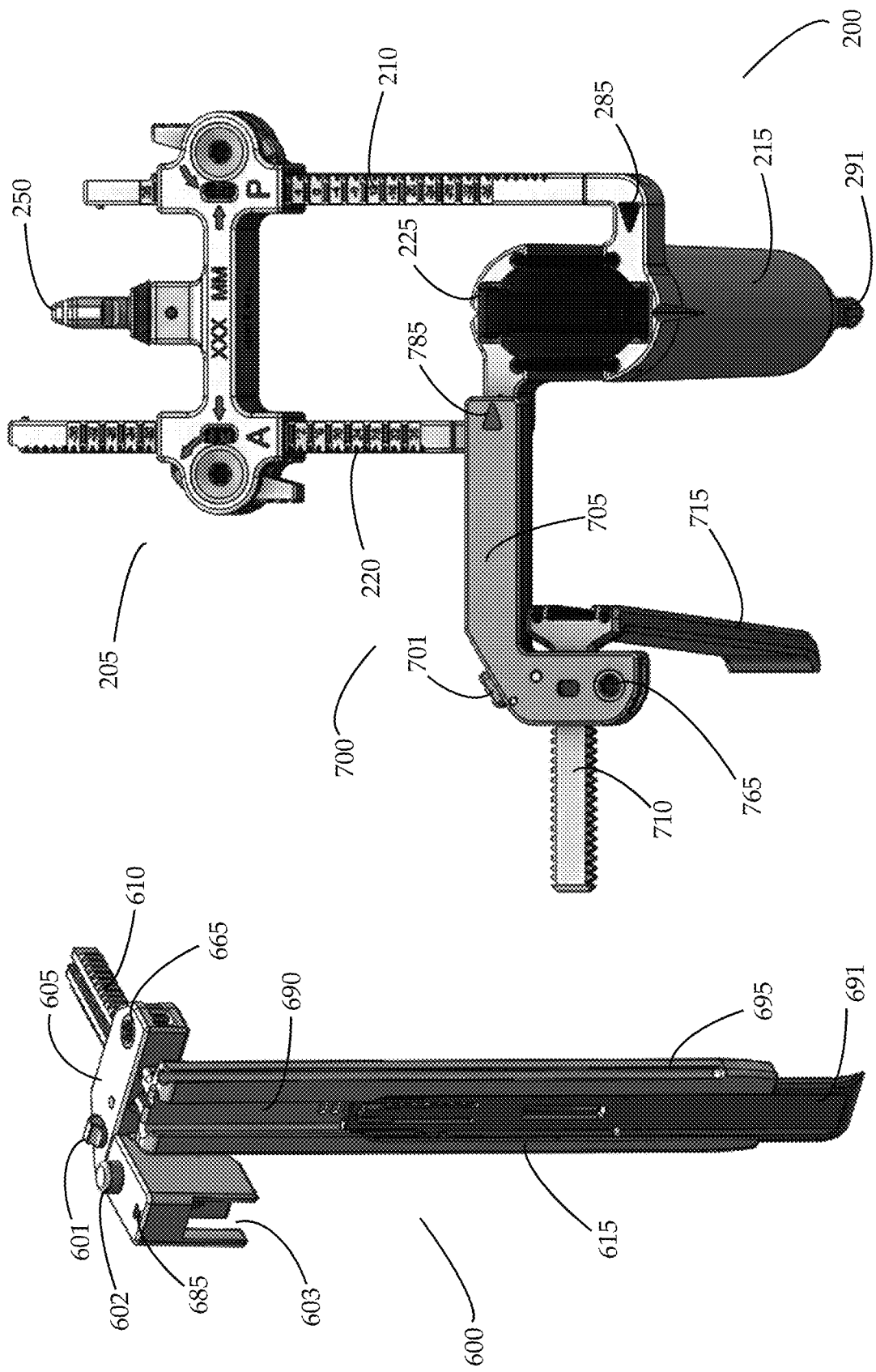
FIG. 12 is a perspective view of yet another embodiment of an auxiliary retractor blade according to the present disclosure.
FIG. 13 is a perspective view of the surgical retractor of FIG. 8 that includes a different embodiment of an auxiliary retractor blade according to the present disclosure.

FIG. 12 illustrates an embodiment of a modular blade assembly 600 that is similar to modular blade assemblies 300, 400, and 500 with a primary difference being that modular blade assembly 600 is configured to be attached to posterior blade arm 210. FIG. 12 also provides a view of receiving area 603 on the underside of base portion 605. It is within this receiving area that a portion of posterior blade arm 210 is inserted. Modular blade assembly 600 also includes a release mechanism 602 configured to trigger disengagement from posterior blade arm 210. As illustrated, release mechanism 602 is a push button mechanism; however, in some embodiments, a toggle mechanism is used as well as any other number of suitable mechanisms. This illustrated embodiment also includes a tissue shim 691 positioned in central channel 690.

FIG. 13 illustrates an embodiment of a modular blade assembly 700 secured to anterior blade arm 220 of retractor 200. Modular blade assembly 700 is similar in many respects to modular blade assemblies 300, 400, 500, and 600 with a key distinction being the elongated portion of base portion 705. Such a design allows for the creation of much larger surgical corridors. For example, where the surgery to be performed involves only a single intervertebral disc, a smaller surgical corridor may be desired to minimize any trauma to surrounding tissue. However, in some surgeries it may be desirable to access two or more vertebral disc spaces through a single approach rather than creating a separate surgical corridor for each disc space. Modular blade assembly 700 is designed for such situations by including the elongated portion, which may be any suitable length to achieve the desired size of surgical corridor.

Figure 14:
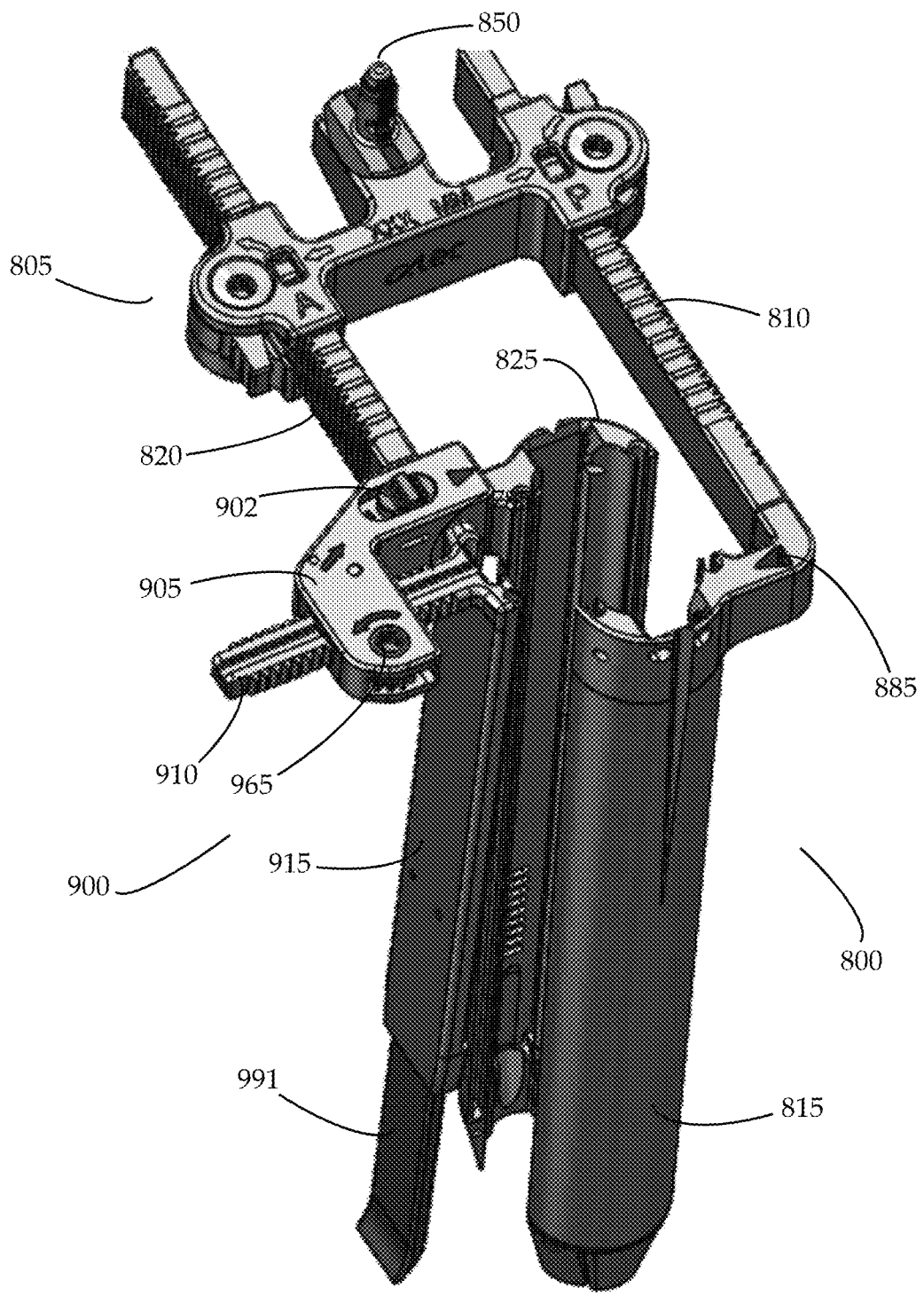
FIG. 14 is a perspective view of a surgical retractor according to the present disclosure that includes an auxiliary retractor blade.

FIG. 14 illustrates an embodiment of a surgical retractor 800 that includes a modular retractor blade 900. Surgical retractor 800 is similar in many aspects to retractors 100 and 200 with a key distinction being that posterior blade 815 and anterior blade 825, together, are oval-shaped rather than circular in shape. Such a variation in shape may be advantageous in certain surgical procedures.

Modular blade assembly 900 is similar in many aspects to modular blade assemblies 300, 400, 500, 600, and 700. Modular blade assembly 900 includes a release mechanism 902 that, in this embodiment, is a toggle mechanism. Release mechanism 902 is configured to maintain modular blade assembly in a locked arrangement with anterior blade arm 820 but to then, when toggled, to allow for modular blade assembly 900 to be easily removed from anterior blade arm 820. Modular blade assembly is also shown as including a tissue shim 991.

Figure 15:
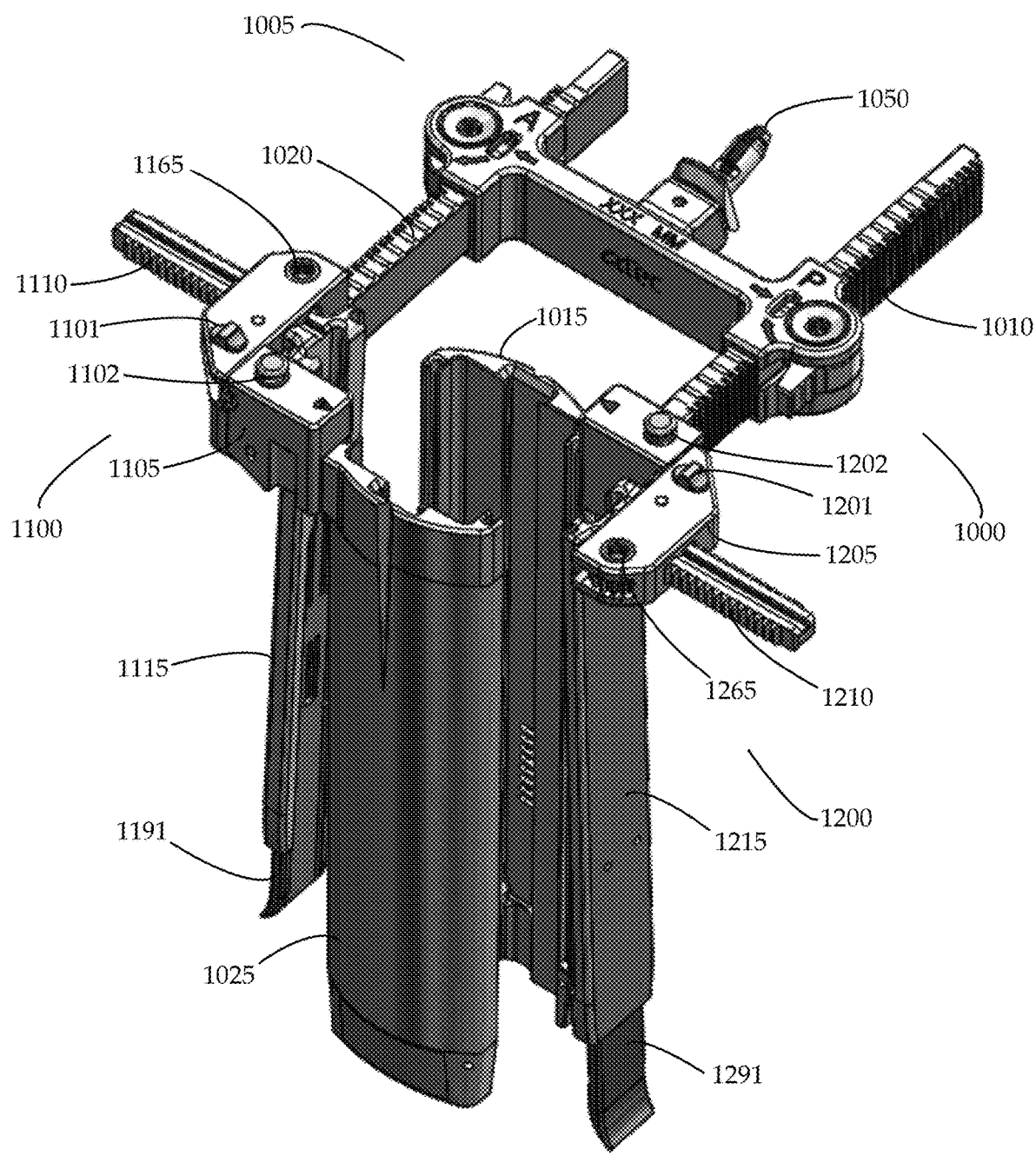
FIG. 15 is a perspective view of a surgical retractor according to the present disclosure that includes two auxiliary retractor blades.

FIG. 15 illustrates an embodiment of a surgical retractor 1000 that includes an anterior modular retractor blade 1100 as well as a posterior modular retractor blade 1200. Surgical retractor 1000 is similar in many aspects to retractors 100, 200, and 800 with a key distinction being that posterior blade 1015 and anterior blade 1025, together, are somewhat rectangular in shape rather than oval-shaped or circular in shape. Such a variation in shape may be advantageous in certain surgical procedures.

Modular blade assembly 900 is similar in many aspects to modular blade assemblies 300, 400, 500, 600, and 700. Modular blade assembly 900 includes a release mechanism 902 that, in this embodiment, is a toggle mechanism. Release mechanism 902 is configured to maintain modular blade assembly in a locked arrangement with anterior blade arm 820 but then, when toggled, to allow for modular blade assembly 900 to be easily removed from anterior blade arm 820. Modular blade assembly is also shown as including a tissue shim 991.

Modular blade assemblies 1100 and 1200 are similar in many aspects to modular blade assemblies 300, 400, 500, 600, 700, and 900. The use of both modular blade assembly 1100 and modular blade assembly 1200 on a single retractor 1000 illustrates how the simple two-blade design of retractor 1000 can easily be modified to establish a surgical corridor with four blades each having one or more channels to accommodate tissue shims, such as tissue shims 1191 and 1291, intradiscal shims, and light cables.

According to some embodiments, it may be desirable to have available for a procedure and/or change during the procedure the types of retractor blades used in retractor 1000. For example, as access to the surgical site is achieved using one or more dilators, a user may want to be able to decide whether the ultimate surgical corridor should be generally circular, generally oval, or generally rectangular and choose retractor blades accordingly.

Accordingly, a suitable retractor system may include (1) a single retractor base portion (such as any one of base portion 105, 205, 805, or 1005), (2) two or more types of retractor blades arms (such as any one of retractor blades 115, 125, 215, 225, 815, 825, 1015, or 1025), where the retractor blades are integral with or unitary with the blade arms, and, (3) optionally, one or more of the various modular retractor assemblies disclosed herein (such as modular retractor blade assemblies 300, 400, 500, 600, 700, 900, 1100, or 1200). Some embodiments of a retractor system may exhibit additional modularity with retractor blades of differing lengths. Some embodiments of a retractor system may exhibit even more modularity with retractor blades that are not integral to the blade arms, such that any suitable or desirable blade shape/size/length may be attached to and removed from a retractor arm that is engaged to a retractor base portion.

According to this disclosure, some exemplary methods of using the surgical retractors disclosed herein include creating an access path through a patient's skin to a surgical site, inserting a pair of retractor blades through the skin, advancing the retractor blades toward the surgical site, and separating the blades from each other to establish a surgical corridor for performing a surgical procedure at the surgical site. Creating an access path may include one or more of the following: (a) after creating an incision in the skin at desired location, advancing a guide wire toward the surgical site; and (b) advancing over the guide wire one or more dilators so to sequentially enlarge the access path. In some embodiments, the one or more dilators are in electrical communication with a neural monitoring system configured to detect nerves that may be along or near the access path. In some embodiments, the retractor blades are already connected to a retractor base portion or may be connected to a retractor base portion after having been advanced toward the surgical site. In some embodiments, the retractor base portion is then attached a support structure, such as an A-arm that is attached to a surgical table. Separating the blades from each other may be achieved by moving one or both blades, which movement may be achieved either by simply pulling the blades apart or by using an adjustment mechanism to adjust the position of one or both blades relative to the retractor base portion. In some embodiments, after the retractor blades have been separated, it may be desirable to either further enlarge the surgical corridor or provide additional barriers to reduce or prevent the encroachment of surrounding tissue into the surgical corridor. In such situations, a modular blade assembly may be used by inserting the retractor blade of the modular blade assembly down into the surgical corridor until the modular blade assembly can be secured to one of the retractor arms of the existing retractor. If additional enlargement or an additional barrier is desired, another modular blade assembly may be used in a similar manner to the first but secured to the other retractor arm.

EMBODIMENTS

The following embodiments are provided as examples only of specific configurations, materials, arrangements, etc. contemplated by the authors of this disclosure:

Embodiment 1. A surgical retractor comprising:
a base portion comprising first and second extensions, the first extension having a first receiving area, the second extension having a second receiving area, and one or more engagement portions;
a posterior retractor blade with proximal and distal ends, the posterior retractor blade having a first retractor arm extending from the proximal end, the first retractor arm configured to be slidingly received by the first receiving area of the base portion; and
an anterior retractor blade with proximal and distal ends, the anterior retractor blade having a second retractor arm extending from the proximal end, the second retractor arm configured to be slidingly received by the second receiving area of the base portion;
wherein the posterior and anterior retractor blades together create an adjustable surgical corridor; and
wherein the posterior and anterior retractor blades are independently adjustable relative to the base portion.

Embodiment 2. The surgical retractor of Embodiment 1 or 2, wherein at least one of the first and second receiving areas comprises a ratchet mechanism configured to lock the first or second retractor arm in position relative to the base portion as the first or second retractor arm is translated through the first or second receiving area.

Embodiment 3. The surgical retractor of Embodiment 2, wherein the first or second retractor arm comprises ratchet teeth along an exterior surface, the ratchet teeth being configured to engage the ratchet mechanism.

Embodiment 4. The surgical retractor of Embodiment 2 or 3, wherein the ratchet mechanism comprises a release lever that when pressed causes the ratchet mechanism to disengage from the first or second retractor arm to allow free movement of the first or second retractor arm through the first or second receiving area.

Embodiment 5. The surgical retractor of Embodiment 1, 2, 3, or 4, wherein at least one of the first and second receiving areas comprises an advancement mechanism that when rotated adjusts the position of the first or second retractor arm relative to the base portion.

Embodiment 6. The surgical retractor of Embodiment 1, 2, 3, 4, or 5, wherein at least one of the posterior and anterior retractor blades is integral with the first or second retractor arm.

Embodiment 7. The surgical retractor of Embodiment 1, 2, 3, 4, 5, or 6, wherein at least one of the posterior and anterior retractor blades is functionally integral with the first or second retractor arm, respectively.

Embodiment 8. The surgical retractor of Embodiment 1, 2, 3, 4, 5, 6, or 7, wherein at least one of (a) the posterior retractor blade and first retractor arm and (b) anterior retractor blade and second retractor arm is unitary.

Embodiment 9. The surgical retractor of Embodiment 1, 2, 3, 4, 5, 6, 7, or 8, wherein at least one of (a) the posterior retractor blade and first retractor arm and (b) anterior retractor blade and second retractor arm is formed of a single material.

Embodiment 10. The surgical retractor of Embodiment 1, 2, 3, 4, 5, 6, 7, 8, or 9, wherein the posterior retractor blade defines an axis that is substantially orthogonal to an axis defined by the first retractor arm; and wherein the anterior retractor blade defines an axis that is substantially orthogonal to an axis defined by the second retractor arm.

Embodiment 11. The surgical retractor of Embodiment 10, wherein the respective axes of the posterior and anterior retractor blades are substantially parallel to each other and remain substantially parallel as the posterior and anterior retractor blades are independently adjusted relative to the base portion so as to adjust the size of the surgical corridor.

Embodiment 12. The surgical retractor of Embodiment 10 or 11, wherein the respective axes of the posterior and anterior retractor blades are substantially parallel to each other and remain so as the posterior and anterior retractor blades are adjusted relative to each other.

Embodiment 13. The surgical retractor of Embodiment 1, 2, 3, 4, 5, 6, 7, 8, 9, 10, 11, or 12, wherein at least one of the posterior and anterior retractor blades comprises at least one alignment feature at its proximal end, the alignment feature configured to provide an indication of the orthogonality of the surgical retractor relative to a surgical site.

Embodiment 14. The surgical retractor of Embodiment 13, wherein the alignment feature is radiographically identifiable.

Embodiment 15. The surgical retractor of Embodiment 13 or 14, wherein the alignment feature comprises a through hole in the proximal end of the first or second retractor.

Embodiment 16. The surgical retractor of Embodiment 13, 14, or 15, wherein the alignment feature comprises a triangular-shaped through hole in the proximal end of the first or second retractor with the triangle pointing toward the surgical corridor.

Embodiment 17. The surgical retractor of Embodiment 13, 14, 15, or 16, wherein the surgical site is a disc space of a patient's spine.

Embodiment 18. The surgical retractor of Embodiment 17, wherein the orthogonality of the surgical retractor relative to the disc space is achieved through a lateral procedure.

Embodiment 19. The surgical retractor of Embodiment 18, wherein surgical retractor is configured to extend at least partially through a portion of the patient's psoas muscle.

Embodiment 20. The surgical retractor of Embodiment 1, 2, 3, 4, 5, 6, 7, 8, 9, 10, 11, 12, 13, 14, 15, 16, 17, 18, or 19, wherein at least one of the posterior and anterior retractor blades comprises a marking to indicate whether it is to be positioned posteriorly or anteriorly.

Embodiment 21. The surgical retractor of Embodiment 1, 2, 3, 4, 5, 6, 7, 8, 9, 10, 11, 12, 13, 14, 15, 16, 17, 18, 19, or 20, wherein the base portion comprises one or more markings to indicate which extension is to be positioned posteriorly or anteriorly.

Embodiment 22. The surgical retractor of Embodiment 1, 2, 3, 4, 5, 6, 7, 8, 9, 10, 11, 12, 13, 14, 15, 16, 17, 18, 19, 20, or 21, wherein the surgical retractor is configured to be used when a patient is in a prone position.

Embodiment 23. The surgical retractor of Embodiment 1, 2, 3, 4, 5, 6, 7, 8, 9, 10, 11, 12, 13, 14, 15, 16, 17, 18, 19, 20, or 21, wherein the surgical retractor is configured to be used when a patient is in a lateral position.

Embodiment 24. The surgical retractor of Embodiment 1, 2, 3, 4, 5, 6, 7, 8, 9, 10, 11, 12, 13, 14, 15, 16, 17, 18, 19, 20, 21, 22, 23, wherein the base portion comprises an anterior face, a posterior face, a top face, and a bottom face; wherein the first and second receiving areas each extend from the anterior face to the posterior face.

Embodiment 25. The surgical retractor of Embodiment 24, wherein the one or more engagement portions extends from the posterior face of the base portion.

Embodiment 26. The surgical retractor of Embodiment 1, 2, 3, 4, 5, 6, 7, 8, 9, 10, 11, 12, 13, 14, 15, 16, 17, 18, 19, 20, 21, 22, 23, 24, or 25, wherein at least one of the first and second retractor arms comprises a top surface comprising markings to indicate a size of the surgical corridor.

Embodiment 27. The surgical retractor of Embodiment 26, wherein at least one of the first and second receiving areas comprises a window for viewing the markings on the first or second retractor arm.

Embodiment 28. The surgical retractor of Embodiment 1, 2, 3, 4, 5, 6, 7, 8, 9, 10, 11, 12, 13, 14, 15, 16, 17, 18, 19, 20, 21, 22, 23, 24, 25, 26, or 27, wherein at least one of the posterior and anterior retractor blades comprises a central channel extending from the proximal end toward the distal end.

Embodiment 29. The surgical retractor of Embodiment 1, 2, 3, 4, 5, 6, 7, 8, 9, 10, 11, 12, 13, 14, 15, 16, 17, 18, 19, 20, 21, 22, 23, 24, 25, 26, 27, or 28, wherein at least one of the posterior and anterior retractor blades comprises at least one lateral channel extending from the proximal end toward the distal end.

Embodiment 30. The surgical retractor of Embodiment 29, further comprising an anchor, the anchor comprising a threaded shank and a projection configured to be received by the at least one lateral channel.

Embodiment 31. The surgical retractor of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, wherein the posterior and anterior retractor blades together form a tube when abutting each other.

Embodiment 32. The surgical retractor of Embodiment 31, wherein the tube substantially encloses the surgical corridor.

Embodiment 33. The surgical retractor of Embodiment 31 or 32, wherein the tube has a cross section that is substantially circular.

Embodiment 34. The surgical retractor of Embodiment 31 or 32, wherein the tube has a cross section that is substantially oval.

Embodiment 35. The surgical retractor of Embodiment 31 or 32, wherein the tube has a cross section that is substantially rectangular.

Embodiment 36. The surgical retractor of Embodiment of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35, wherein the posterior and anterior retractor blades are configured to slide over a dilator.

Embodiment 37. The surgical retractor of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, wherein the posterior and anterior retractor blades form a substantially rectangular surgical corridor.

Embodiment 38. A method of using a surgical retractor, the method comprising:
making an incision in a patient's skin at a position lateral to the patient's spine;
locating a surgical site on the spine;
inserting the posterior and anterior retractor blades of the surgical retractor of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or 37;
advancing the surgical retractor toward the surgical site to create a surgical corridor to access the surgical site;
positioning the distal end of the posterior retractor blade at a posterior position of the surgical site;
anchoring the posterior retractor blade at the posterior position; and
enlarging the surgical corridor.

Embodiment 39. The method of Embodiment 38, wherein locating the surgical site on the spine comprises:
advancing a K-wire toward the surgical site and embedding a distal end of the K-wire into a tissue at the surgical site; and
sequentially advancing an inner dilator and an outer dilator over the K-wire toward the surgical site.

Embodiment 40. The method of Embodiment 39, wherein advancing a K-wire toward the surgical site comprises traversing at least a portion of the psoas muscle.

Embodiment 41. The method of Embodiment 39 or 40, wherein at least one of the inner and outer dilators comprises at least one electrode and is configured to provide neural monitoring as the dilator is advanced toward the surgical site.

Embodiment 42. The method of Embodiment 41, wherein the at least one electrode is configured to provide a plexus map.

Embodiment 43. The method of Embodiment 39, 40, 41, or 42, wherein the inner and outer dilators are circular in cross section.

Embodiment 44. The method of Embodiment 39, 40, 41, or 42, wherein the inner and outer dilators are oval in cross section.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It should also be noted that some of the embodiments disclosed herein may have been disclosed in relation to a particular approach (e.g., lateral); however, other approaches (e.g., anterior, posterior, transforaminal, etc.) are also contemplated.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the embodiments of the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the present disclosure are approximations, the numerical values set forth in the specific examples are reported as precisely as possible. Any numerical value, however, inherently contains certain errors necessarily resulting from the standard deviation found in their respective testing measurements. In one embodiment, the terms "about" and "approximately" refer to numerical parameters within 10% of the indicated range.

The terms "a," "an," "the," and similar referents used in the context of describing the embodiments of the present disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the embodiments of the present disclosure and does not pose a limitation on the scope of the present disclosure. No language in the specification should be construed as indicating any non-claimed element essential to the practice of the embodiments of the present disclosure.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the author(s) of this disclosure for carrying out the embodiments disclosed herein. Of course, variations on these described embodiments will become apparent to those of ordinary skill in the art upon reading the foregoing description. The author(s) expects skilled artisans to employ such variations as appropriate, and the author(s) intends for the embodiments of the present disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the present disclosure unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of this disclosure so claimed are inherently or expressly described and enabled herein.

Furthermore, if any references have been made to patents and printed publications throughout this disclosure, each of these references and printed publications are individually incorporated herein by reference in their entirety.

In closing, it is to be understood that the embodiments disclosed herein are illustrative of the principles of the present disclosure. Other modifications that may be employed are within the scope of this disclosure. Thus, by way of example, but not of limitation, alternative configurations of the embodiments of the present disclosure may be utilized in accordance with the teachings herein. Accordingly, the present disclosure is not limited to that precisely as shown and described.

The invention claimed is:
1. A surgical retractor comprising:
a base portion comprising first and second extensions defining a first axis, the first extension having a first receiving area that is a first passage from a first side of the base portion through to a second side of the base portion that is opposite the first side, the first passage defining a second axis, the second extension having a second receiving area that is a second passage from the first side of the base portion to the second side of the base portion, the second passage defining a third axis parallel to the second axis, and one or more engagement portions, the second and third axes being normal to the first axis;
a posterior retractor blade with proximal and distal ends, the posterior retractor blade having a first retractor arm extending from the proximal end, the first retractor arm configured to be slidingly received by the first receiving area of the base portion so as to be translatable through the first receiving area, the first retractor arm translating along an axis that is normal to the first axis; and
an anterior retractor blade with proximal and distal ends, the anterior retractor blade having a second retractor arm extending from the proximal end, the second retractor arm configured to be slidingly received by the second receiving area of the base portion so as to be translatable through the second receiving area, the second retractor arm translating along an axis that is normal to the first axis;
wherein the posterior and anterior retractor blades together create an adjustable surgical corridor not intersected by the first axis;
wherein the first and second retractor arms are independently adjustable,
wherein at least one of the posterior and anterior retractor blades comprises at least one alignment feature at its proximal end, the alignment feature configured to provide an indication of the orthogonality of the surgical retractor relative to a surgical site; and
wherein the alignment feature comprises a triangular-shaped through hole in the proximal end of the first or second retractor blade with the triangular-shaped through hole pointing toward the surgical corridor.

2. The surgical retractor of claim 1, wherein at least one of the first and second receiving areas comprises an advancement mechanism that when rotated adjusts the position of the first or second retractor arm relative to the base portion.

3. The surgical retractor of claim 1, wherein at least one of the posterior and anterior retractor blades is integral with the first or second retractor arm.

4. The surgical retractor of claim 1, wherein the posterior retractor blade defines an axis that is substantially orthogonal to an axis defined by the first retractor arm; and wherein the anterior retractor blade defines an axis that is substantially orthogonal to an axis defined by the second retractor arm and wherein the respective axes of the posterior and anterior retractor blades are substantially parallel to each other and remain substantially parallel as the posterior and anterior retractor blades are independently adjusted relative to the base portion so as to adjust the size of the surgical corridor.

5. The surgical retractor of claim 1, wherein the alignment feature is radiographically identifiable.

6. The surgical retractor of claim 1, wherein the surgical site is a disc space of a patient's spine and wherein the orthogonality of the surgical retractor relative to the disc space is achieved through a lateral procedure.

7. The surgical retractor of claim 6, wherein the surgical retractor is configured to extend at least partially through at least a portion of a patient's psoas muscle.

8. The surgical retractor of claim 1, wherein the surgical retractor is configured to be used when a patient is in a prone position.

9. The surgical retractor of claim 1, wherein at least one of the first and second retractor arms comprises a top surface comprising markings to indicate a size of the surgical corridor.

10. The surgical retractor of claim 1, wherein at least one of the posterior and anterior retractor blades comprises a central channel extending from the proximal end toward the distal end.

11. The surgical retractor of claim 1, wherein at least one of the posterior and anterior retractor blades comprises at least one lateral channel extending from the proximal end toward the distal end.

12. The surgical retractor of claim 1, wherein the posterior and anterior retractor blades are configured to slide over a dilator.

13. A surgical retractor comprising:
a base portion comprising first and second extensions defining a first axis, the first extension having a first receiving area that is a first passage from a first side of the base portion through to a second side of the base portion that is opposite the first side, the first passage defining a second axis, the second extension having a second receiving area that is a second passage from the first side of the base portion to the second side of the base portion, the second passage defining a third axis parallel to the second axis, and one or more engagement portions, the second and third axes being normal to the first axis;
a posterior retractor blade with proximal and distal ends, the posterior retractor blade having a first retractor arm extending from the proximal end, the first retractor arm configured to be slidingly received by the first receiving area of the base portion so as to be translatable through the first receiving area, the first retractor arm translating along an axis that is normal to the first axis; and
an anterior retractor blade with proximal and distal ends, the anterior retractor blade having a second retractor arm extending from the proximal end, the second retractor arm configured to be slidingly received by the second receiving area of the base portion so as to be translatable through the second receiving area, the second retractor arm translating along an axis that is normal to the first axis;
wherein the posterior and anterior retractor blades together create an adjustable surgical corridor not intersected by the first axis;
wherein the first and second retractor arms are independently adjustable; and
wherein the posterior and anterior retractor blades together form a tube when abutting each other.

14. The surgical retractor of claim 13, wherein the tube substantially encloses the surgical corridor.

15. The surgical retractor of claim 13, wherein the posterior and anterior retractor blades form a substantially rectangular surgical corridor.

16. The surgical retractor of claim 13, wherein the tube has a cross section that is substantially circular.

17. The surgical retractor of claim 13, wherein the tube has a cross section that is substantially oval.

18. The surgical retractor of claim 13, wherein at least one of the posterior and anterior retractor blades comprises at least one alignment feature at its proximal end, the alignment feature configured to provide an indication of the orthogonality of the surgical retractor relative to a surgical site.

19. The surgical retractor of claim 18, wherein the alignment feature comprises a triangular-shaped through hole in the proximal end of the first or second retractor blade with the triangular-shaped through hole pointing toward the surgical corridor.

20. The surgical retractor of claim 13, wherein at least one of the first and second receiving areas comprises an advancement mechanism that when rotated adjusts the position of the first or second retractor arm relative to the base portion.

21. The surgical retractor of claim 13, wherein at least one of the posterior and anterior retractor blades is integral with the first or second retractor arm.

22. The surgical retractor of claim 13, wherein the posterior retractor blade defines an axis that is substantially orthogonal to an axis defined by the first retractor arm; and wherein the anterior retractor blade defines an axis that is substantially orthogonal to an axis defined by the second retractor arm and wherein the respective axes of the posterior and anterior retractor blades are substantially parallel to each other and remain substantially parallel as the posterior and anterior retractor blades are independently adjusted relative to the base portion so as to adjust the size of the surgical corridor.

23. The surgical retractor of claim 18, wherein the alignment feature is radiographically identifiable.

24. The surgical retractor of claim 18, wherein the alignment feature comprises a through hole in the proximal end of the first or second retractor blade.

25. The surgical retractor of claim 18, wherein the surgical site is a disc space of a patient's spine and wherein the orthogonality of the surgical retractor relative to the disc space is achieved through a lateral procedure.

26. The surgical retractor of claim 25, wherein the surgical retractor is configured to extend at least partially through at least a portion of a patient's psoas muscle.

27. The surgical retractor of claim 13, wherein the surgical retractor is configured to be used when a patient is in a prone position.

28. The surgical retractor of claim 13, wherein the posterior and anterior retractor blades are configured to slide over a dilator.

* * * * *